United States Patent
Sjölund

(10) Patent No.: US 12,415,091 B2
(45) Date of Patent: Sep. 16, 2025

(54) RADIOTHERAPY TREATMENT PLANS USING DIFFERENTIABLE DOSE FUNCTIONS

(71) Applicant: Elekta AB (publ), Stockholm (SE)

(72) Inventor: Jens Olof Sjolund, Stockholm (SE)

(73) Assignee: Elekta AB (publ), Stockholm (SE)

( * ) Notice: Subject to any disclaimer, the term of this patent is extended or adjusted under 35 U.S.C. 154(b) by 1098 days.

(21) Appl. No.: 17/305,831

(22) Filed: Jul. 15, 2021

(65) Prior Publication Data

US 2021/0339049 A1   Nov. 4, 2021

Related U.S. Application Data

(63) Continuation of application No. 16/512,938, filed on Jul. 16, 2019, now Pat. No. 11,097,128.

(51) Int. Cl.
| | | |
|---|---|---|
| *A61N 5/10* | (2006.01) | |
| *G06N 3/084* | (2023.01) | |
| *G06N 20/00* | (2019.01) | |
| *G16H 20/40* | (2018.01) | |
| *G16H 50/20* | (2018.01) | |

(52) U.S. Cl.
CPC ......... *A61N 5/1039* (2013.01); *A61N 5/1031* (2013.01); *A61N 2005/1034* (2013.01)

(58) Field of Classification Search
CPC ................ A61N 5/1039; A61N 5/1031; A61N 2005/1034; A61N 5/103; G06N 20/00; G06N 3/084; G16H 20/40; G16H 50/20
See application file for complete search history.

(56) References Cited

U.S. PATENT DOCUMENTS

| | | |
|---|---|---|
| 11,097,128 B2 | 8/2021 | Sjölund |
| 2009/0316858 A1 | 12/2009 | Nord et al. |
| 2010/0213394 A1 | 8/2010 | Fieres |
| 2012/0020460 A1 | 1/2012 | Witten et al. |
| 2014/0275703 A1 | 9/2014 | Sobotta |
| 2016/0140300 A1 | 5/2016 | Purdie et al. |
| 2016/0346566 A1 | 12/2016 | Mercier et al. |

(Continued)

FOREIGN PATENT DOCUMENTS

| | | |
|---|---|---|
| AU | 2020312642 | 7/2022 |
| CN | 109843377 | 6/2019 |

(Continued)

OTHER PUBLICATIONS

"Australian Application Serial No. 2020312642, First Examination Report mailed Jun. 15, 2022", 2 pgs.

(Continued)

*Primary Examiner* — Carrie R Dorna
*Assistant Examiner* — Joshua D Lannu
(74) *Attorney, Agent, or Firm* — Schwegman Lundberg & Woessner, P.A.

(57) ABSTRACT

Techniques for generating a radiotherapy treatment plan parameter are provided. The techniques include receiving radiotherapy treatment plan information; processing the radiotherapy treatment plan information to estimate one or more radiotherapy treatment plan parameters based on a process that depends on the output of a subprocess that estimates a derivative of a dose calculation; and generating a radiotherapy treatment plan using the estimated one or more radiotherapy treatment plan parameters.

16 Claims, 10 Drawing Sheets

(56) References Cited

U.S. PATENT DOCUMENTS

| | | | |
|---|---|---|---|
| 2019/0030370 A1* | 1/2019 | Hibbard | ............... A61N 5/1067 |
| 2019/0030371 A1 | 1/2019 | Han | |
| 2019/0175952 A1 | 6/2019 | Hissoiny | |
| 2021/0016109 A1 | 1/2021 | Sjölund | |

FOREIGN PATENT DOCUMENTS

| | | |
|---|---|---|
| CN | 114423494 | 4/2022 |
| EP | 3302701 A1 | 4/2018 |
| JP | 2018108284 | 7/2018 |
| WO | WO-2017156316 A1 | 9/2017 |
| WO | WO-2019027924 A1 | 2/2019 |
| WO | WO-2021009055 A1 | 1/2021 |

OTHER PUBLICATIONS

"Australian Application Serial No. 2020312642, Voluntary Amendment filed Jun. 6, 2022", 14 pgs.

"Australian Application Serial No. 2020312642, Response filed Jun. 17, 2022 to First Examination Report mailed Jun. 15, 2022", Claims not amended in response filed, 1 pg.

"Chinese Application Serial No. 202080064465.7, Voluntary Amendment filed Jun. 22, 2022", w English Claims, 13 pgs.

"European Application Serial No. 20739660.7, Response to Communication pursuant to Rules 161 and 162 filed Jun. 29, 2022", 20 pgs.

"Japanese Application Serial No. 2022-502847, Notification of Reasons for Refusal mailed Jul. 5, 2022", w English Translation, 4 pgs.

"Japanese Application Serial No. 2022-502847, Response filed Aug. 8, 2022 to Notification of Reasons for Refusal mailed Jul. 5, 2022", w English Claims, 7 pgs.

"International Application Serial No. PCT EP2020 069582, International Preliminary Report on Patentability mailed Jan. 27, 2022", 9 pgs.

"U.S. Appl. No. 16/512,938, Corrected Notice of Allowability mailed Jun. 1, 2021", 2 pgs.

"U.S. Appl. No. 16/512,938, Non Final Office Action mailed Feb. 5, 2021", 11 pgs.

"U.S. Appl. No. 16/512,938, Notice of Allowance mailed May 12, 2021", 13 pgs.

"U.S. Appl. No. 16/512,938, Response filed Apr. 21, 2021 to Non Final Office Action mailed May 2, 2021", 12 pgs.

"International Application Serial No. PCT/EP2020/069582, International Search Report mailed Oct. 5, 2020", 6 pgs.

"International Application Serial No. PCT/EP2020/069582, Written Opinion mailed Oct. 5, 2020", 7 pgs.

Fries, Christian P., "Stochastic automatic differentiation: automatic differentiation for Monte-Carlo simulations", Quantitative Finance 19.6, (2019), 1043-1059.

Gelman, Andrew, "Method of moments using Monte Carlo simulation", Journal of Computational and Graphical Statistics 4.1, (1995), 36-54.

Martin, Soukup, et al., "A pencil beam algorithm for intensity modulated proton therapy derived from Monte Carlo simulations; A pencil beam algorithm for intensity modulated proton therapy", Physics in Medicine and Biology, Institute of Physics Publishing, Bristol GB, vol. 50, No. 21, (Nov. 7, 2015), 5089-5104.

Sirignano, Justin, et al., "DGM: A deep learning algorithm for solving partial differential equations", Journal of computational physics 375, (2018), 1339-1364.

Sjolund, Jens, et al., "A linear programming approach to inverse planning in Gamma Knife radiosurgery", Medical physics 46.4, (2019), 1533-1544.

"Chinese Application Serial No. 202080064465.7, Office Action mailed Aug. 1, 2022", W English Translation, 18 pgs.

"Chinese Application Serial No. 202080064465.7, Response filed Oct. 24, 2022 to Office Action mailed Aug. 1, 2022", w English Claims, 13 pgs.

* cited by examiner

RADIOTHERAPY TREATMENT PLANS USING DIFFERENTIABLE DOSE FUNCTIONS

CLAIM FOR PRIORITY

This application is a continuation of U.S. application Ser. No. 16/512,938, filed Jul. 16, 2019, which is hereby incorporated by reference in its entirety.

TECHNICAL FIELD

This disclosure relates generally to generating a radiation therapy or radiotherapy treatment plan.

BACKGROUND

Radiotherapy is used to treat cancers and other ailments in mammalian (e.g., human and animal) tissue. The direction and shape of the radiation beam should be accurately controlled to ensure the tumor receives the prescribed radiation, and the placement of the beam should be such as to minimize damage to the surrounding healthy tissue (often called the organ(s) at risk (OARs)). Treatment planning can be used to control radiation beam parameters, and a radiotherapy device effectuates a treatment by delivering a spatially varying dose distribution to the patient.

Traditionally, for each patient, a radiation therapy treatment plan ("treatment plan") may be created using an optimization technique based on clinical and dosimetric objectives and constraints (e.g., the maximum, minimum, and mean doses to the tumor and critical organs). The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming, trial-and-error process that is complicated by the various OARs, because as the number of OARs increases (e.g., 21 are commonly segmented in a head-and-neck treatment), so does the complexity of the process. OARs distant from a tumor may be easily spared from radiation, while OARs close to or overlapping a target tumor may be difficult to spare.

Segmentation may be performed to identify the OARs and the area to be treated (for example, a planning target volume (PTV)). After segmentation, a dose plan may be created for the patient indicating the desirable amount of radiation to be received by the, one or more, PTV (e.g., target) and/or the OARs. A PTV may have an irregular volume and may be unique as to its size, shape, and position. A treatment plan can be calculated after optimizing a large number of plan parameters to ensure that enough dose is provided to the PTV(s) while as low a dose as possible is provided to surrounding healthy tissue. Therefore, a radiation therapy treatment plan may be determined by balancing efficient control of the dose to treat the tumor against sparing any OAR. Typically, the quality of a radiation treatment plan may depend upon the level of experience of the planner. Further complications may be caused by anatomical variations between patients.

Overview

In some embodiments, a computer-implemented method, non-transitory computer readable medium, and a system comprising a memory and processor are provided for generating a radiotherapy treatment plan parameter by: receiving, by processor circuitry, radiotherapy treatment plan information; processing, by the processor circuitry, the radiotherapy treatment plan information to estimate one or more radiotherapy treatment plan parameters based on a process that depends on the output of a subprocess that estimates a derivative of a dose calculation, wherein the derivative of the dose calculation is used in an optimization process or a machine learning model that is based on a loss function, wherein the derivative of the dose calculation is computed with respect to at least one of one or more radiation parameters or one or more geometry parameters of a radiotherapy treatment device; and generating, by the processor circuitry, a radiotherapy treatment plan using the estimated one or more radiotherapy treatment plan parameters.

In some embodiments, the radiotherapy treatment plan information includes at least one of a magnetic resonance (MR) image, a cone-beam computed tomography (CBCT) image, a computed tomography (CT) image, a dose distribution, a segmentation map and a distance map.

In some embodiments, the estimated one or more radiotherapy treatment plan parameters comprises at least one of a synthetic computed tomography (sCT) image and a dose distribution.

In some embodiments, processing the radiotherapy treatment plan information comprises processing the radiotherapy treatment plan information with a machine learning model to generate the one or more estimated radiotherapy treatment plan parameters, wherein the machine learning model is trained to establish a relationship between a plurality of training radiotherapy treatment plan information and a plurality of training radiotherapy treatment plan parameters, based on dose calculations using the plurality of training radiotherapy treatment plan information, wherein the machine learning model includes a deep neural network, wherein the plurality of training radiotherapy treatment plan information comprises at least one of a training MR image, a training CBCT image, a training CT image, a first training dose distribution, a training segmentation map or a training distance map, and wherein the plurality of training radiotherapy treatment plan parameters comprises at least one of a training synthetic computed tomography (sCT) image or a second training dose distribution.

In some embodiments, the machine learning model is trained by: obtaining a first batch of training data pairs comprising a given set of training radiotherapy treatment plan information and a set of corresponding training radiotherapy treatment plan parameters; processing the given set of training radiotherapy treatment plan information with the machine learning model to generate an intermediate radiotherapy treatment plan parameter; computing a derivative of the loss function based on the intermediate radiotherapy treatment plan parameter; and updating parameters of the machine learning model based on the computed derivative of the loss function.

In some embodiments, the computer-implemented method, non-transitory computer readable medium, and the system perform operations comprising: computing a first dose based on the set of corresponding training radiotherapy treatment plan parameters; computing a second dose based on the intermediate radiotherapy treatment plan parameter; and applying the first and second doses to the loss function before computing the derivative of the loss function.

In some embodiments, the dose calculation includes at least one or a combination of a Monte Carlo simulation or a deterministic calculation using a point kernel convolution algorithm, a pencil kernel algorithm, or a Boltzmann equation solver.

In some embodiments, the optimization process comprises a radiotherapy treatment plan optimization problem that comprises decision variables specifying at least one of an isocenter location or a beam angle for the radiotherapy treatment device.

In some embodiments, wherein the derivative of the dose calculation is a first-order derivative. In some implementations, the first-order derivative is not a constant value.

In some embodiments, the subprocess that estimates a derivative comprises an automatic differentiation process.

The above overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
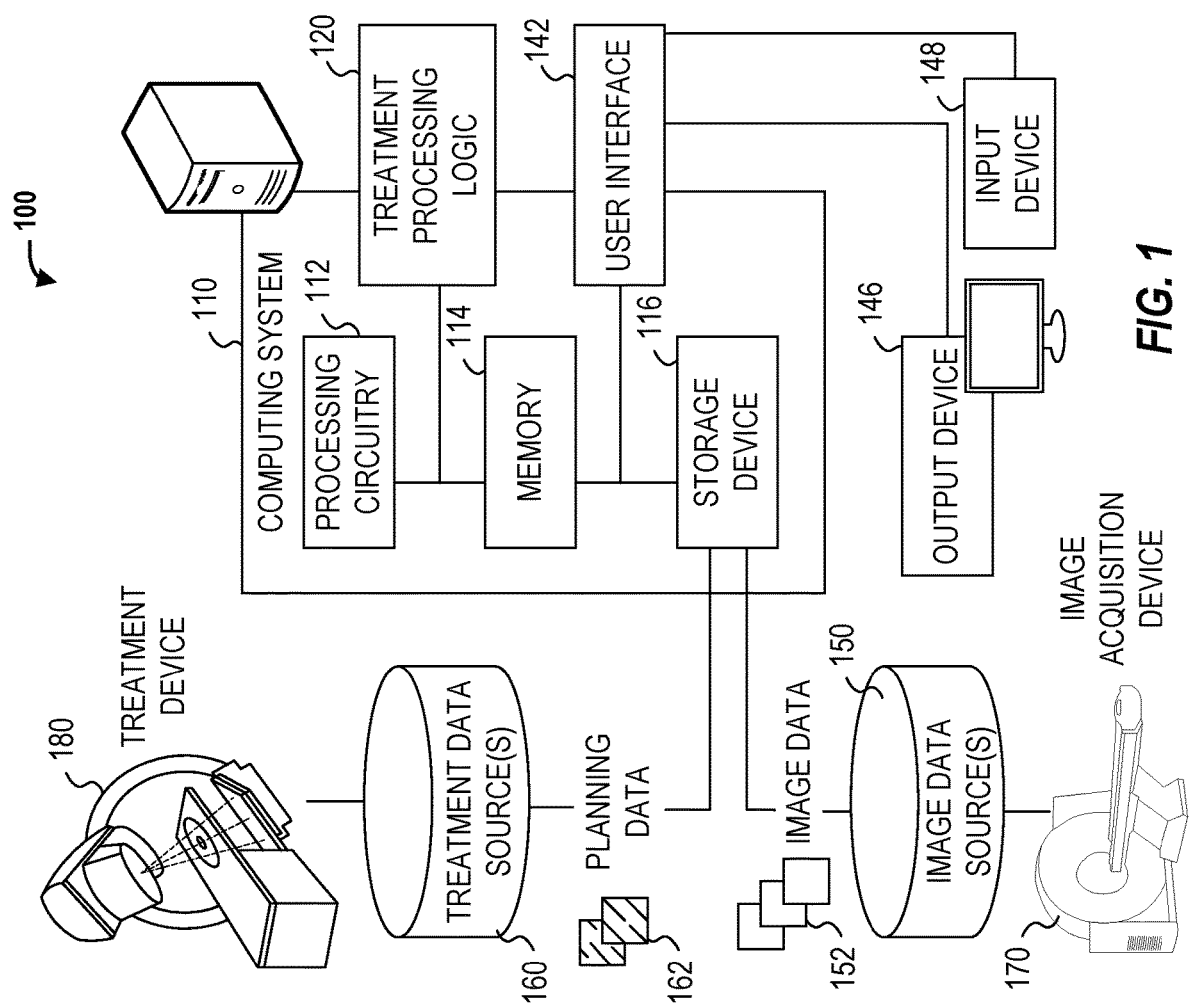
FIG. 1 illustrates an exemplary radiotherapy system adapted for performing treatment plan generation processing, according to some examples of the disclosure.

The present disclosure includes various techniques to generate radiotherapy treatment plans by using a machine learning (ML) model or solving an optimization problem based on a derivative of a dose calculation. As one example, the ML model can be trained to estimate one or more parameters of the radiotherapy treatment plan (e.g., a synthetic CT image) from radiotherapy treatment plan information (e.g., a CT or MR image) based on a loss function that takes into account a derivative of a dose. As another example, one or more parameters (e.g., a constraint and or a decision variable) of an optimization problem can consider a derivative of a dose to generate a solution to the optimization problem to provide one or more parameters of the radiotherapy treatment plan (e.g., radiotherapy device parameters or control points). The technical benefits include reduced computing processing times to generate radiotherapy treatment plans and solving radiotherapy treatment plan optimization problems and accompanying improvements in processing, memory, and network resources used to generate radiotherapy treatment plans and solve radiotherapy treatment plan optimization problems. These radiotherapy treatment plans may be applicable to a variety of medical treatment and diagnostic settings or radiotherapy treatment equipment and devices. Accordingly, in addition to these technical benefits, the present techniques may also result in many apparent medical treatment benefits (including improved accuracy of radiotherapy treatment, reduced exposure to unintended radiation, and the like).

Radiotherapy is one of the primary methods for treating cancer and is recommended for over 50% of all cancer patients. Treatment plans are created through a complex design process involving a mathematical optimization problem that captures the desirable characteristics of the dose delivery—typically requiring a sufficiently high dose to the target while minimizing the dose to healthy tissue. The overall structure of the optimization problem is the same for most forms of radiotherapy, including linac-based treatments (3D-CRT, IMRT, VMAT), proton treatments, Gamma Knife radiosurgery, and brachytherapy. The end result is the radiotherapy device configuration (e.g., control points) required to deliver the dose distribution.

Simulation of the absorbed radiation dose in a volume (e.g., dose calculations) is typically an important factor in generating radiotherapy treatment plans. The dose is used as a reliable and verifiable link between the chosen treatment parameters and the observed clinical outcome for a specified treatment technique. The result of a careful treatment plan optimization is a set of treatment variables, such as prescribed dose level for the tumor, the number of therapeutic beams, their angles of incidence, and a set of intensity amplitudes. Several dose calculation processes exist including stochastic processes, such as Monte Carlo simulation, and deterministic processes such as point kernel convolution algorithms, pencil kernel algorithms, or Boltzmann equation solvers.

Deterministic analytical dose calculations can be divided into two types: point kernel convolution algorithms and pencil kernel algorithms. Point kernel methods first calculate the total energy released per mass (TERMA) in the patient with a raytrace method and a subsequent convolution (or superposition) with the point kernel to model the dose distribution from the generated electrons and scattered photons. The convolution with the point kernel redistributes the TERMA into the correct dose distribution and is the most time-consuming step. A common implementation of the convolution step is the collapsed cone algorithm.

The Boltzmann transport equation (BTE) is the governing equation which describes the macroscopic behavior of radiation particles (neutrons, photons, electrons, etc.) as they travel through and interact with matter. The LBTE is the linearized form of the BTE, which assumes that radiation particles only interact with the matter they are passing through, and not with each other, and is valid for conditions without external magnetic fields. For a given volumetric domain of matter, subject to a radiation source, under the above conditions the solution to the LBTE would give an "exact" description of the dose within the domain. However, since closed form solutions (analytic solutions) to the LBTE can only be obtained for a few simplified problems, the LBTE is typically solved in an open form, or non-analytic, manner. There are two general approaches to obtaining open form solutions to the LBTE. The first approach is the widely known Monte Carlo method. Monte Carlo methods do not explicitly solve the LBTE; they indirectly obtain the solution to this equation. The second approach is to explicitly solve the LBTE using numerical methods.

Current planning software typically solve the minimization problem using standard mathematical optimization methods. These can be slow, causing unnecessary waiting for patients and clinicians. Future applications utilizing real-time imaging could even require real-time treatment planning, which cannot be performed using conventional optimization problem solvers. Typical optimization problem solvers take into account dose after generating a solution which results in certain inefficiencies if the dose fails to meet certain constraints. Namely, optimization problem solvers fail to consider a dose calculation in generating solutions resulting in inaccurate and ineffective treatment plan parameters. Also, certain ML models are used to generate some or all parameters of the radiotherapy treatment plan but such ML models also fail to consider dose calculations. As a result, the parameters provided by the ML models may end up being inaccurate and fail to satisfy certain dose constraints resulting in inefficiencies.

The disclosed techniques address these challenges and increase the speed and efficiency at which radiotherapy treatment plan is generated by taking into account a derivative of a dose calculation in training a ML model or optimizing an optimization problem. In some implementations, the disclosed techniques consider dose calculations given a set of treatment variables to verify or update radiotherapy treatment plan parameters and settings. For example, an ML model can be trained based on a dose based loss function to generate a synthetic CT image from an MRI or cone-beam computed tomography (CBCT) image to use in treatment plan optimization. As another example, one or more parameters of a radiotherapy treatment plan optimization problem can be based on a derivative of a dose calculation to provide beam angle optimization (for Linacs) or isocenter selection (for Gamma Knife). As another example, control points of a radiotherapy device can be estimated by applying an ML model that is trained based on a dose based loss function to a medical image (e.g., MRI, CT, CBCT, and/or sCT image). As another example, a computationally costly dose calculation can be processed more efficiently and faster using an ML model that is trained to replicate the dose calculation of the computationally costly function. By increasing the speed and accuracy at which radiotherapy treatment plan parameters are generated, the disclosed techniques may enable real-time treatment planning to be performed and reduce wait time for patients and clinicians.

Specifically, the disclosed techniques receive radiotherapy treatment plan information and process the radiotherapy treatment plan information to estimate one or more radiotherapy treatment plan parameters based on a process that depends on the output of a subprocess that estimates a derivative of a dose calculation. A radiotherapy treatment plan is generated using the estimated one or more radiotherapy treatment plan parameters. In general, the disclosed techniques can be applied to a radiotherapy treatment plan application that utilizes a derivative of dose with respect to a treatment variable.

As used herein, the term "derivative" refers to any of derivative, subderivative, gradient, subgradient, directional derivative, Jacobian, Fréchet derivative, higher-order derivative, differential operator, Radon-Nikodym derivative, Schwarzian derivative, Wirtinger derivative, H-derivative, covariant derivative, variational derivative, functional derivative, and/or any combination thereof.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters. Specifically, the following processing operations may be implemented as part of the treatment processing logic 120. It will be understood, however, that many variations and use cases of the following trained models and treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more private and/or public medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160.

As an example, the radiotherapy processing computing system 110 can be configured to receive a treatment goal of a subject (e.g., from one or more MR images) and generate a radiotherapy treatment plan by executing instructions or data from the treatment processing logic 120, as part of operations to generate treatment plans to be used by the treatment device 180 and/or for output on device 146. In an embodiment, the treatment processing logic 120 solves an optimization problem and/or applies an ML model to the treatment goal to generate the radiotherapy treatment plan. In an example, the treatment processing logic 120 receives radiotherapy treatment plan information and processes the radiotherapy treatment plan information to estimate one or more radiotherapy treatment plan parameters based on a process that depends on the output of a subprocess that estimates a derivative of a dose calculation. The subprocess that estimates the derivative of the dose calculation can be performed based on any one or combination of techniques including symbolic differentiation; numerical differentiation (e.g., finite differences); and automatic differentiation by applying the chain rule on the elementary arithmetic operations that underpin every computer program, no matter how complicated. Then the treatment processing logic 120 generates a radiotherapy treatment plan using the estimated one or more radiotherapy treatment plan parameters.

A generic radiotherapy treatment plan optimization problem can be defined as Equation 1:

$$\underset{x \in X}{\text{minimize}} f(x) \qquad (1)$$

$$\text{subject to } x \in \Omega$$

where $f: X \rightarrow \mathbb{R}$ is the objective function, $x \in X$ is the decision variables and $\Omega \subseteq X$ is the set of feasible variables. In general, the function $f$ can be nonlinear and the set $\Omega$ non-convex. The optimization problems are typically solved using some form of iterative scheme. For example, in case $f$ is smooth and convex, and $\Omega$ is convex, then the projected gradient scheme could be used to solve eq. (1) and reads as follows:

$$x_{n+1} = \text{proj}_\Omega(x_n - \eta \nabla f(x_n))$$

where $\text{proj}_\Omega: X \to X$ is the projection onto $\Omega$, $\eta \in \mathbb{R}$ is a stepsize and $\nabla f: X \to X$ the gradient. While these algorithms are typically provably convergent (e.g., given enough time (and correct parameter choices), the algorithm will converge to a minimizer). According to the disclosed techniques, one or more parameters of the optimization problem of Equation 1 can be computed or provided by a derivative of a dose calculation. In doing so, updates to the decision variables of the radiotherapy treatment plan optimization problem are more accurate with respect to the dose to a patient which makes finding a solution faster.

Particularly, the disclosed embodiments enhance the speed and efficiency of solving the optimization problem and increase the accuracy of the solution by utilizing a dose calculation as one or more of the parameters of the optimization problem. In general, a dose D depends on two broad categories of treatment variables, any one of which can be considered by the parameters of Equation 1. Such treatment variables include radiation parameters $\Psi$ and geometry parameters $\Omega$. The radiation parameters $\Psi$ can include the number of therapeutic beams, angles of incidence, intensity amplitudes, isocentre locations, collimator configurations, dwell times, and so forth. The geometry parameters SI can include patient position, shape, density, material decomposition, and so forth. In some implementations, the dose is represented by Equation 2 which can be included as one or more of the parameters of the optimization problem of Equation 1:

$$D = D(\Psi, \Omega) \qquad (2)$$

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, training data, software programs (e.g., image processing software, image or anatomical visualization software, artificial intelligence (AI) or ML implementations and algorithms such as provided by deep learning models, ML models, and neural networks (NNs), etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor rather than a general-purpose processor. The processing circuitry 112 may include one or more known processing devices, such as a microprocessor from the Pentium™, Core™ Xeon™, or Itanium® family manufactured by Intel™, the Turion™, Athlon™ Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry-based) or software-based processor (for example, a multi-core design or a plurality of processors each having a multi-core design). The processing circuitry 112 can execute sequences of transitory or non-transitory computer program instructions, stored in memory 114, and accessed from the storage device 116, to perform various operations, processes, and methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, one or more ML model(s) or technique(s) parameters, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, one or more AI model data (e.g., weights and parameters of the ML model(s) of the disclosed embodiments), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images) for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data as a result of a treatment plan generated by the treatment processing logic 120. The image data source 150 may also provide or host the imaging data for use in the treatment processing logic 120.

In an example, computing system 110 may communicate with treatment data source(s) 160 and input device 148 to generate pairs of a plurality of training radiotherapy treatment plan information and a plurality of training radiotherapy treatment plan parameters; pairs of training MR and/or CBCT images and training sCT images; pairs of training MR, CT, sCT, CBCT images, segmentation and distance maps and training radiotherapy device control points; and pairs of training dose computation functions and training dose distributions.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120 to generate a treatment plan. Particularly, treatment processing logic 120 receives an optimization problem that is based on a derivative of a dose computation expression and/or an ML model that is trained based on a derivative of a dose computation expression. The treatment processing logic 120 solves the received optimization problem to generate one or more parameters of a treatment plan, applies the ML model to radiotherapy treatment plan information to estimate one or more parameters of a treatment plan, and/or applies the ML model to radiotherapy treatment plan information to estimate an intermediate dose distribution of a dose computation function to simplify computation of dose distribution using the intermediate dose distribution estimate.

In addition, the processing circuitry 112 may utilize software programs to generate intermediate data such as updated parameters to be used, for example, by a NN model, machine learning model, treatment processing logic 120 or other aspects involved with generation of a treatment plan as discussed herein. Further, such software programs may utilize the treatment processing logic 120 to produce new or updated treatment plan parameters for deployment to the treatment data source 160 and/or presentation on output device 146, using the techniques further discussed herein. The processing circuitry 112 may subsequently then transmit the new or updated treatment plan parameters via a communication interface and the network to the treatment device 180, where the radiation therapy plan will be used to treat a patient with radiation via the treatment device 180, consistent with results of the trained ML model implemented by the treatment processing logic 120 (e.g., according to the processes discussed below in connection with FIG. 3).

In the examples herein, the processing circuitry 112 may execute software programs that invoke the treatment processing logic 120 to implement functions of ML, deep learning, NNs, and other aspects of artificial intelligence for treatment plan generation from an input radiotherapy medical information (e.g., CT image, MR image, and/or sCT image and/or dose information). For instance, the processing circuitry 112 may execute software programs that train, analyze, predict, evaluate, and generate a treatment plan parameter from received radiotherapy medical information as discussed herein.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data (for example, training images, ground truth images, contoured images, and dose images). In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, including control points of a radiotherapy treatment device, such as couch position, beam intensity, beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information (e.g., control points) may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may use to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT or MRI volume. Such 2D slices can be acquired by the image acquisition device 170 in "near real time" while a patient is undergoing radiation therapy treatment (for example, when using the treatment device 180 (with "near real time" meaning acquiring the data in at least milliseconds or less)).

The treatment processing logic 120 in the radiotherapy processing computing system 110 implements a ML model, which involves the use of a trained (learned) ML model. This ML model may be provided by a NN trained as part of a NN model. One or more teacher ML models may be provided by a different entity or at an off-site facility relative to treatment processing logic 120 and is accessible by issuing one or more queries to the off-site facility.

Supervised machine learning (ML) algorithms or ML models or techniques can be summarized as function approximation. Training data consisting of input-output pairs of some type (e.g., pairs of a plurality of training radiotherapy treatment plan information and a plurality of training radiotherapy treatment plan parameters; pairs of training MR and/or CBCT images and training sCT images; pairs of training MR, CT, sCT, CBCT images, segmentation and distance maps and training radiotherapy device control points; and pairs of training dose computation functions and training dose distributions) are acquired from, e.g., expert clinicians or prior optimization plan solvers and a function is "trained" to approximate this mapping. Some methods involve NNs. In these, a set of parametrized functions $A_\theta$ are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem such as Equation 3:

$$\min_\theta \sum_{m=1}^{M} \|A_\theta(x_m) - y_m\|^2 \quad (3)$$

The minimization problem of Equation 3 that is used to train the network can be based on a loss function that includes a derivative of a dose calculation.

Once the network has been trained (e.g., $\theta$ has been selected), the function $A_\theta$ can be applied to any new input. For example, a never-before-seen radiotherapy treatment plan information (e.g., an MR and/or CBCT image) can be fed into $A_\theta$, and one or more radiotherapy treatment plan parameters (e.g., an sCT image) are estimated. As another example, a never-before-seen MR, CT, sCT, CBCT image, segmentation and distance map can be fed into $A_\theta$, and one or more radiotherapy device control points are estimated. As another example, a never-before-seen dose computation function parameters can be fed into $A_\theta$, and one or more intermediate dose distributions are estimated.

Simple NNs consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier, the number of input layer nodes typically equals the number of features for each of a set of objects being sorted into classes, and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function $y=f(x)$ including non-linear functions. In ML, an assumption is that the training and test data are both generated by the same data-generating process, $p_{data}$, in which each $\{x_i, y_i\}$ sample is identically and independently distributed (i.i.d.). In ML, the goals are to minimize the training error and to make the difference between the training and test errors as small as possible. Underfitting occurs if the training error is too large; overfitting occurs when the train-test error gap is too large. Both types of performance deficiency are related to model capacity: large capacity may fit the training data very well but lead to overfitting, while small capacity may lead to underfitting.

Figure 2A:
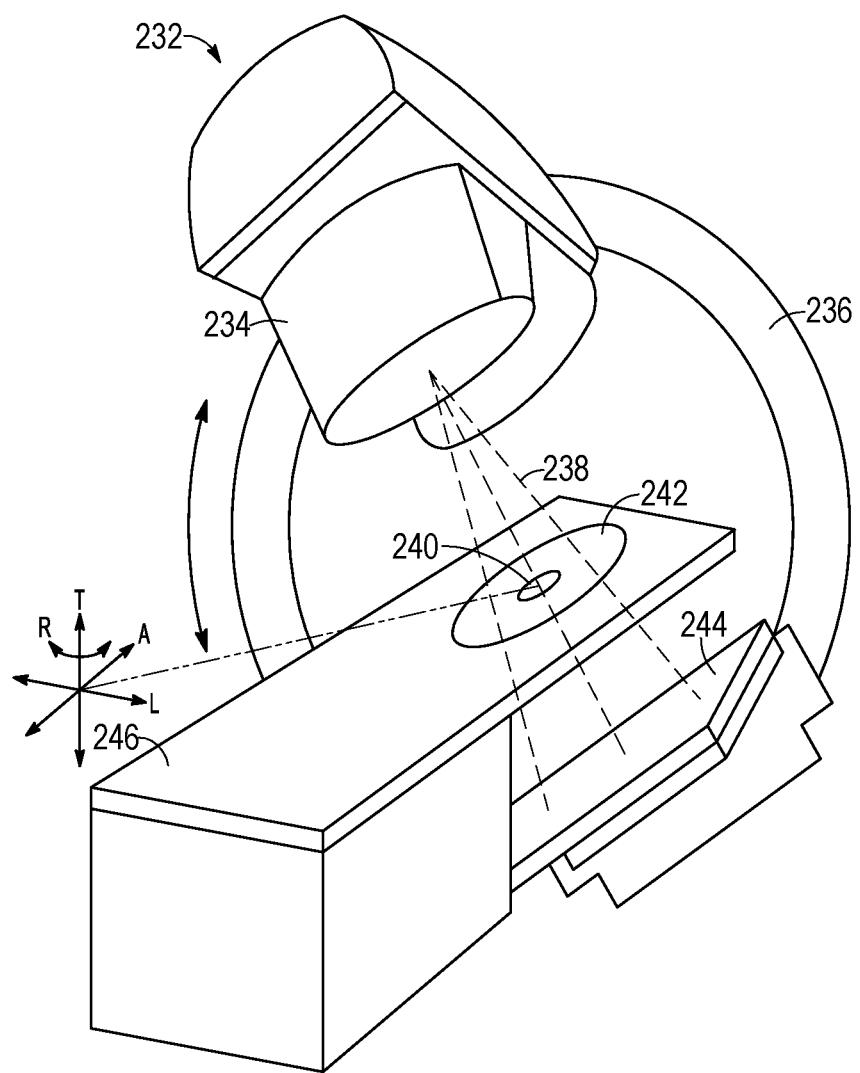
FIG. 2A illustrates an exemplary image-guided radiotherapy device, according to some examples of the disclosure.

FIG. 2A illustrates an exemplary image-guided radiation therapy device 232 that includes a radiation source, such as an X-ray source or a linear accelerator, a couch 246, an imaging detector 244, and a radiation therapy output 234. The radiation therapy device 232 may be configured to emit a radiation therapy beam 238 to provide therapy to a patient. The radiation therapy output 234 can include one or more attenuators or collimators, such as a MLC.

As an example, a patient can be positioned in a region 242, supported by the treatment couch 246, to receive a radiation therapy dose according to a radiation therapy treatment plan. The radiation therapy output 234 can be mounted or attached to a gantry 236 or other mechanical support. One or more chassis motors (not shown) may rotate the gantry 236 and the radiation therapy output 234 around the couch 246 when the couch 246 is inserted into the treatment area. In an example, gantry 236 may be continuously rotatable around couch 246 when the couch 246 is inserted into the treatment area. In another example, gantry 236 may rotate to a predetermined position when the couch 246 is inserted into the treatment area. For example, the gantry 236 can be configured to rotate the therapy output 234 around an axis ("A"). Both the couch 246 and the radiation therapy output 234 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 246's movements or rotations in order to properly position the patient in or out of the radiation therapy beam 238, according to a radiation therapy treatment plan. Both the couch 246 and the gantry 236 are independently moveable from one another in multiple degrees of freedom, which allows the patient to be positioned such that the radiation therapy beam 238 can precisely target the tumor.

The coordinate system (including axes A, T, and L) can have an origin located at an isocenter 240. The isocenter 240 can be defined as a location where the central axis of the radiation therapy beam 238 intersects the origin of a coordinate axis, such as to deliver a prescribed radiation dose to a location on or within a patient. Alternatively, the isocenter 240 can be defined as a location where the central axis of the radiation therapy beam 238 intersects the patient for various rotational positions of the radiation therapy output 234 as positioned by the gantry 236 around the axis A.

Gantry 236 may also have an attached imaging detector 244. The imaging detector 244 is preferably located opposite to the radiation source (output 234) and, in an example, the imaging detector 244 can be located within a field of the therapy beam 238. The imaging detector 244 can be mounted on the gantry 236, preferably opposite the radiation therapy output 234, so as to maintain alignment with the radiation therapy beam 238. The imaging detector 244 rotates about the rotational axis as the gantry 236 rotates. In an example, the imaging detector 244 can be a flat panel detector (e.g., a direct detector or a scintillator detector). In this manner, the imaging detector 244 can be used to monitor the radiation therapy beam 238, or the imaging detector 244 can be used for imaging the patient's anatomy, such as portal imaging. The control circuitry of radiation therapy device 232 may be integrated within the radiotherapy system 100 or remote from it.

In an illustrative example, one or more of the couch 246, the therapy output 234, or the gantry 236 can be automatically positioned, and the therapy output 234 can establish the therapy beam 238 according to a specified dose for a particular therapy delivery instance. A sequence of therapy deliveries can be specified according to a radiation therapy treatment plan, such as using one or more different orientations or locations of the gantry 236, couch 246, or therapy output 234. The therapy deliveries can occur sequentially but can intersect in a desired therapy locus on or within the patient, such as at the isocenter 240. A prescribed cumulative dose of radiation therapy can thereby be delivered to the therapy locus while damage to tissue nearby the therapy locus can be reduced or avoided.

Thus, FIG. 2A specifically illustrates an example of a radiation therapy device 232 operable to provide radiotherapy treatment to a patient consistent with or according to a radiotherapy treatment plan, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, and the like, as would be recognized by one of ordinary skill in the art.

Figure 2B:
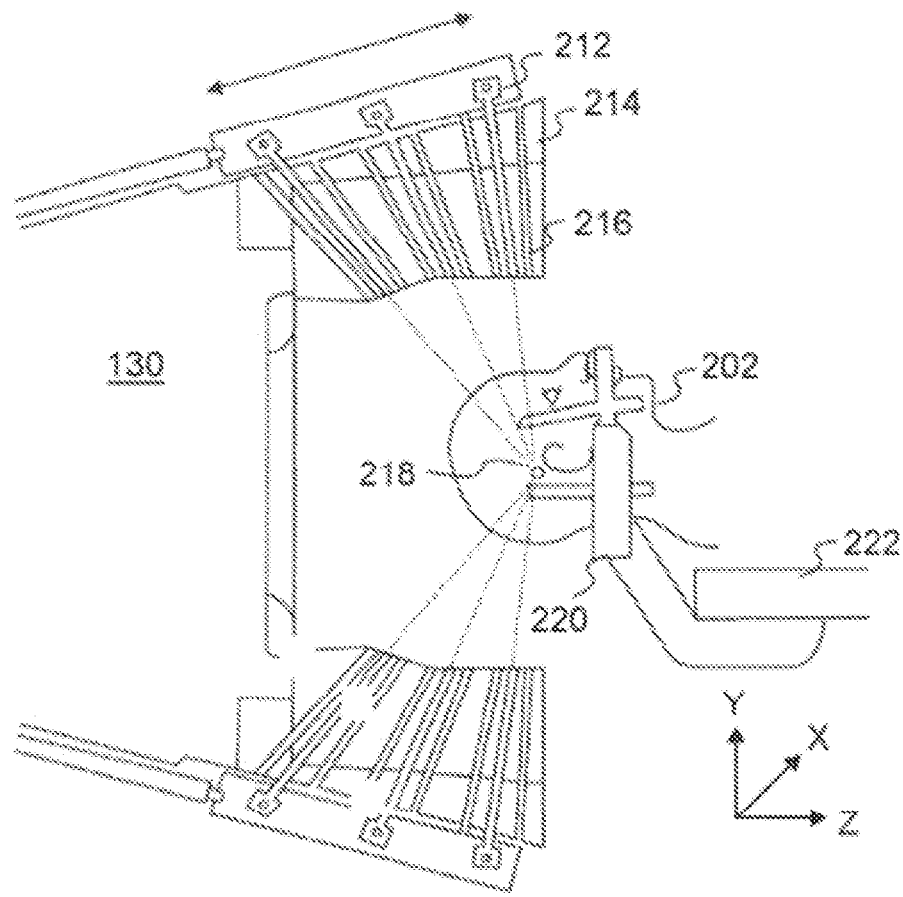
FIG. 2B illustrates a radiation therapy device, a Gamma Knife, according to some examples of the disclosure.

FIG. 2B illustrates a radiotherapy device 130, a Gamma Knife in which the present disclosure can be used. A patient 202 may wear a coordinate frame 220 to keep stable the patient's body part (e.g. the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

Figure 3:
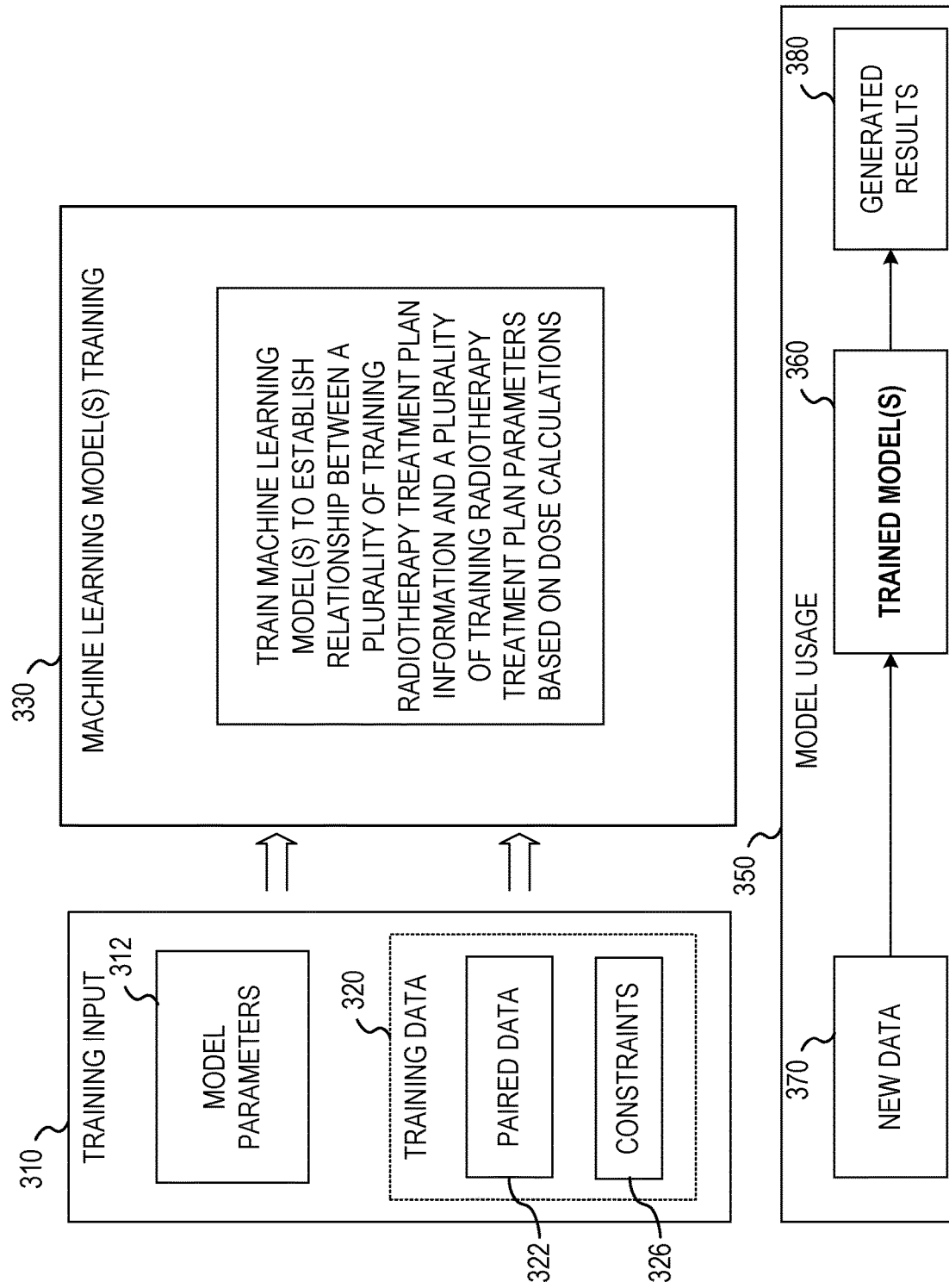
FIG. 3 illustrates an exemplary data flow for training and use of a machine learning technique based on a derivative of a dose, according to some examples of the disclosure.

FIG. 3 illustrates an exemplary data flow for training and use of machine learning model(s) based on a derivative of a dose, according to some examples of the disclosure. The data flow includes training input 310, ML model(s) (technique(s)) training 330, and model(s) usage 350.

Training input 310 includes model parameters 312 and training data 320 which may include paired training data sets 322 (e.g., input-output training pairs) and constraints 326. Model parameters 312 stores or provides the parameters or coefficients of corresponding ones of machine learning models $\hat{A}_\theta$. During training, these parameters 312 are adapted based on the input-output training pairs of the training data sets 322. After the parameters 312 are adapted (after training), the parameters are used by trained treatment models 360 to implement the respective one of the trained machine learning models $\hat{A}_\theta$ on a new set of data 370.

Training data 320 includes constraints 326 which may define the physical constraints of a given radiotherapy device. The paired training data sets 322 may include sets of input-output pairs, such as a pairs of a plurality of training radiotherapy treatment plan information and a plurality of training radiotherapy treatment plan parameters; pairs of training MR and/or CBCT images and training sCT images; pairs of training MR, CT, sCT, CBCT images, segmentation and distance maps and training radiotherapy device control points; and pairs of training dose computation functions and training dose distributions. Some components of training input 310 may be stored separately at a different off-site facility or facilities than other components.

Machine learning model(s) training 330 trains one or more machine learning techniques $\hat{A}_\theta$ based on the sets of input-output pairs of paired training data sets 322. For example, the model training 330 may train the ML model parameters 312 by minimizing a first loss function based on one or more derivatives of a dose computation. Particularly, the ML model can be applied to radiotherapy treatment plan information to estimate one or more radiotherapy treatment plan parameters. In some implementations, a derivative of a loss function is computed based on the one or more radiotherapy treatment plan parameters and parameters of the ML model are updated based on the computed derivative of the loss function. In some implementations, the radiotherapy treatment plan parameters are applied to a dose computation function, such as one defined by Equation 2, to compute a first dose. A gradient or derivative of a loss function to which the computed first dose is applied is computed and parameters of the ML model are updated based on the computed gradient or derivative. In some implementations supervised training approaches are used in which a second dose is computed based on training radiotherapy treatment plan parameters corresponding to the received radiotherapy treatment plan. In such cases, both dose computations are applied to the loss function for which the gradient or derivative of the loss function is computed and parameters of the ML model are updated based on the computed gradient or derivative. In unsupervised ML model training, only the first dose is applied to the loss function for which the gradient or derivative is computed and evaluated against a metric to update parameters of the ML model.

The result of minimizing the loss function for multiple sets of training data trains, adapts, or optimizes the model parameters 312 of the corresponding ML models. In this way, the ML model is trained to establish a relationship between a plurality of training radiotherapy treatment plan information and a plurality of training radiotherapy treatment plan parameters.

The ML model is trained in one implementation according to supervised learning techniques to estimate radiotherapy treatment plan parameters from radiotherapy treatment plan information. Supervised learning techniques assume that $x_f^* = \arg\min_x f(x)$ is known from previously computing radiotherapy treatment plan parameters corresponding to radiotherapy treatment plan information. In such cases, to train the ML model $\Lambda_\theta$, a plurality of training radiotherapy treatment plan information are retrieved together with their corresponding training radiotherapy treatment plan parameters. The ML model is applied to a first batch of training radiotherapy treatment plan information to estimate a given set of radiotherapy treatment plan parameters. The batch of the training radiotherapy treatment plan information can be used to train the ML model with the same parameters of the ML model and may range from one training radiotherapy treatment plan information to all of the training radiotherapy treatment plan information. In some implementations, the output or result of the ML model is used to compute a first dose or derivative of a first dose (e.g., by computing a derivative, such as using an automatic differentiation process, of Equation 2 that includes the output or result of the ML model). Additionally, the radiotherapy treatment plan parameters corresponding to the batch of radiotherapy treatment plan information is used to compute a second dose or derivative of a second dose in a similar manner. The first dose (or derivative of the first dose) and the second dose (or derivative of the second dose) are applied to a loss function and a gradient or derivative of the loss function with the applied doses is computed. Based on the gradient or derivative of the loss function, updated parameters for the ML model are computed. In some implementations, a derivative of the loss function is computed based on the radiotherapy treatment plan parameters and parameters of the ML model are updated based on the computed derivative of the loss function. For example, a computation of dL/dD (derivative of the loss function with respect to a dose calculation) is performed given the current set of estimated radiotherapy treatment plan parameters and corresponding set of radiotherapy treatment plan parameters. Another computation of dD/d(ML model parameters) (derivative of dose calculation with respect to ML model parameters) is performed and the ML model parameters are updated based on the current ML model parameters and the computation of dD/d(ML model parameters). The ML model is then applied with the updated parameters to a second batch of training radiotherapy treatment plan information to again estimate a given set of parameters of a radiotherapy treatment plan to compute doses and apply the doses to a loss function. Parameters of the ML model are again updated and iterations of this training process continue for a specified number of iterations or epochs or until a given convergence criteria has been met.

The ML model is trained in one implementation according to supervised learning techniques to estimate an sCT image from one or more medical images (e.g., an MR image, CT image, and/or a CBCT image). In such cases, to train the ML model $\Lambda_\theta$, a plurality of training medical images are retrieved together with their corresponding training sCT images and/or training CT images. The ML model is applied to a first batch of training medical images to estimate a given set of sCT images. The batch of the training medical images can be used to train the ML model with the same parameters of the ML model and may range from one training medical image to all of the training medical images. In some implementations, the output or result of the ML model is used to compute a first dose or derivative of a first dose (e.g., by computing a derivative, such as using an automatic differentiation process, of Equation 2 that includes the output or result of the ML model). Additionally, the sCT images corresponding to the batch of medical images is used to compute a second dose or derivative of a second dose in a similar manner. The first dose (or derivative of the first dose) and the second dose (or derivative of the second dose) are applied to a loss function and a gradient or derivative of the loss function with the applied doses is computed. Based on the gradient or derivative of the loss function, updated parameters for the ML model are computed. In some implementations, a derivative of the loss function is computed based on the sCT image and parameters of the ML model are updated based on the computed derivative of the loss function. For example, a computation of dL/dD (derivative of the loss function with respect to a dose calculation) is performed given the current set of estimated sCT images and corresponding set of training sCT or CT images. Another computation of dD/d(ML model parameters) (derivative of dose calculation with respect to ML model parameters) is performed and the ML model parameters are updated based on the current ML model parameters and the computation of dD/d(ML model parameters). The ML model is then applied with the updated parameters to a second batch of training medical images to again estimate a given set of sCT images to compute doses and apply the doses to a loss function. Parameters of the ML model are again updated and iterations of this training process continue for a specified number of iterations or epochs or until a given convergence criteria has been met.

The ML model is trained in one implementation according to supervised learning techniques to estimate a dose distribution or radiotherapy treatment plan from a CT image, a segmentation map and/or a distance map. In such cases, to train the ML model $\Lambda_\theta$, a plurality of training CT image, a segmentation map and/or a distance map are retrieved together with their corresponding training dose distribution or radiotherapy treatment plan. The ML model is applied to a first batch of training CT image, a segmentation map and/or a distance map to estimate a given set of dose distribution or radiotherapy treatment plan. The batch of the training CT image, a segmentation map and/or a distance map can be used to train the ML model with the same parameters of the ML model and may range from one training CT image, a segmentation map and/or a distance map to all of the training CT images, a segmentation maps and/or a distance maps. In some implementations, the output or result of the ML model is used to compute a first dose or derivative of a first dose (e.g., by computing a derivative, such as using an automatic differentiation process, of Equation 2 that includes the output or result of the ML model). Additionally, the dose distribution or radiotherapy treatment plan corresponding to the batch of a CT image, a segmentation map and/or a distance map is used to compute a second dose or derivative of a second dose in a similar manner. The first dose (or derivative of the first dose) and the second dose (or derivative of the second dose) are applied to a loss function and a gradient or derivative of the loss function with the applied doses is computed. Based on the gradient or derivative of the loss function, updated parameters for the ML model are computed. In some implementations, a derivative of the loss function is computed based on the dose distribution or radiotherapy treatment plan and parameters of the ML model are updated based on the computed derivative of the loss function. For example, a computation of dL/dD (derivative of the loss function with respect to a dose calculation) is performed given the current set of estimated dose distribution or radiotherapy treatment plan and corresponding set of training dose distribution or radiotherapy treatment plan. Another computation of dD/d (ML model parameters) (derivative of dose calculation with respect to ML model parameters) is performed and the ML model parameters are updated based on the current ML model parameters and the computation of dD/d(ML model parameters). The ML model is then applied with the updated parameters to a second batch of training a CT image, a segmentation map and/or a distance map to again estimate a given set of dose distribution or radiotherapy treatment plan to compute doses and apply the doses to a loss function. Parameters of the ML model are again updated and iterations of this training process continue for a specified number of iterations or epochs or until a given convergence criteria has been met.

The ML model is trained in one implementation according to supervised learning techniques to estimate a second dose calculation from a first dose calculation. In such cases, to train the ML model $\Lambda_\theta$, a plurality of training first dose calculations are retrieved together with their corresponding training second dose calculations. The ML model is applied to a first batch of training first dose calculations to estimate a given set of second dose calculations. The batch of the training first dose calculation can be used to train the ML model with the same parameters of the ML model and may range from one training first dose calculation to all of the training first dose calculations. The estimated second dose calculation and the retrieved training second dose calculation, corresponding to the training first dose calculation, are applied to a loss function and a gradient or derivative of the loss function with the applied dose calculations is computed. Based on the gradient or derivative of the loss function, updated parameters for the ML model are computed. The ML model is then applied with the updated parameters to a second batch of training first dose calculations to again estimate a given set of second dose calculations and apply the dose calculations to a loss function. Parameters of the ML model are again updated and iterations of this training process continue for a specified number of iterations or epochs or until a given convergence criteria has been met.

The ML model trained in one implementation according to unsupervised learning techniques, wherein the true radiotherapy treatment parameters corresponding to radiotherapy treatment plan information are not used (regardless of whether they are known or not). In such cases, to train the ML model $\Lambda_\theta$, a plurality of training radiotherapy treatment plan information for other patients (and/or that include synthetically generated radiotherapy treatment plan information) are retrieved. The ML model is applied to a first batch of the training radiotherapy treatment plan information to estimate a given set of radiotherapy treatment plan parameters (e.g., sCT images, a radiotherapy treatment plan, a dose calculation, a dose distribution). The batch of the training radiotherapy treatment plan information can be used to train the ML model with the same parameters of the ML model and may range from one training radiotherapy treatment plan information to all of the training radiotherapy treatment plan information. The output or result of the ML model is used to compute a dose or derivative of a dose based on Equation 2 which is evaluated using a loss function to obtain feedback on the loss/utility of the current iteration. Based on a gradient or derivative of this loss function, updated parameters for the ML model are computed. The ML model is then applied with the updated parameters to a second batch of training radiotherapy treatment plan information to again estimate a given set of radiotherapy treatment plan parameters. Parameters of the ML model are again updated and iterations of this training process continue for a specified number of iterations or epochs or until a given convergence criteria has been met.

In some embodiments, the derivative of the dose (the first dose or the second dose) includes a first order derivative. In some implementations, the first order derivative is not a constant value.

Specifically, the ML model is trained in a supervised or unsupervised manner based on the loss function such that a derivative of a dose computed based on a set of radiotherapy treatment plan parameters estimated by the ML model for a given radiotherapy treatment plan information satisfies a stopping criteria after a specified fixed number of iterations. Specifically, the ML model is trained until a stopping criteria is met (e.g., a maximum number of iterations has been reached, a decrease in objective value is achieved, a step length is met, etc.) or when a dose or derivative of a dose computed based on an output of the ML model is within a specified threshold error. In this way, this trained ML model can be applied to a new radiotherapy treatment plan information to estimate one or more radiotherapy treatment plan parameters.

After the machine learning model $\hat{A}_\theta$ (sometimes referred to as $\Lambda_\theta$) is trained, new data 370, including one or more patient input parameters (e.g., radiotherapy treatment plan information, such as a medical image), may be received. The trained machine learning technique $\hat{A}_\theta$ may be applied to the new data 370 to generate generated results 380 including one or more estimated parameters (e.g., an sCT image) of the radiotherapy treatment plan.

In some embodiments, an estimated sCT image is used to compute a derivative of a dose expression. The purpose of the sCT image is often to check whether the dose deviations are acceptable if the treatment planned beforehand is delivered to the current patient anatomy and position. An important criteria for the sCT image is thus that it results in an accurate description of the dose distribution that would result from delivering the treatment. Typical systems fail to tune the sCT image generation explicitly to achieve this objective of an accurate description of the dose distribution. Some approaches have settled for a proxy where the sCT image is tuned to have image intensities (Hounsfield Units) that are as similar as possible to a corresponding CT image.

As such, in some implementations, differentiable dose calculations are used to improve sCT image generation. To do so, a ML model is trained to take an MR image as the input x and output y as a sCT image (a volume with values given in Hounsfield Units, hence a geometry parameter of Equation 2), where the training objective is to minimize the dose deviations (in L2 norm) on a training database of old treatment plans. That means the ML model is trained in a supervised machine learning algorithm $f_\theta(x)$ by selecting the parameters θ to minimize a dose based empirical loss L given by Equation 4:

$$L(f_\theta(x),y) = E_{\Psi,\Omega}[\|D(\Psi,f_\theta(x)) - D(\Psi,y)\|_2^2] \quad (4)$$

If the dose calculation is differentiable, the ML model can be trained with this loss in and end-to-end fashion and the chain rule can be used to compute the derivate of the loss according to Equation 5:

$$\frac{dL}{d\theta} = \frac{dL}{dD}\left(\frac{\partial D}{\partial \Psi}\frac{d\Psi}{d\theta} + \frac{\partial D}{\partial \Omega}\frac{d\Omega}{d\theta}\right) = \frac{dL}{dD}\frac{\partial D}{\partial f}\frac{df}{d\theta} \quad (5)$$

where the second equality holds in this example because $$\frac{d\Psi}{d\theta} = 0$$

Ψ doesn't depend on θ) and $\Omega = f_\theta(x)$. The training results in a fixed set of parameters θ* for the model. When presented with a previously unseen MR image $\hat{x}$, a synthetic CT image can be generated by applying the learned function $f_{\theta^*}(\hat{x})$. A detailed diagram of this example is shown and described below in connection with FIG. 7.

In some embodiments, the ML model that is trained based on a derivative of a dose expression can be used to perform automatic treatment planning. In automatic treatment planning, the aim is to automatically generate treatments plans based only on inputs such as medical images and delineated structures (structure sets). The most successful strategies try to replicate the treatment intent, typically expressed in terms of the dose distribution or some quantity derived from it, using some element of learning based on previous treatment plans. However, learning the dose distribution is only a halfway-solution, because to deliver the treatment, a machine configuration that achieves the treatment plan is needed. The step of finding the machine configurations can be considered as a form of inverse problem, which is typically approached by formulating and solving an optimization problem. So far, the performance degradation that results when moving from prediction to realizable plan has mostly been ignored.

As such, according to some embodiments, by explicitly incorporating knowledge of the forward model, e.g., the dose calculation, it becomes possible to efficiently use supervised learning to train a ML model that maps directly from medical images to a machine configuration (or control points).

Specifically, to train such a ML model, let x be inputs in the form of a CT scan and a collection of distance maps from a number of different structures, and let y be machine parameters in the form of a collection of apertures and irradiation angles. The dose calculation uses both the CT images and the machine parameters to simulate the resulting dose distribution, e.g., $D = \hat{D}(x, y)$. A neural network can be used with parameters θ to describe the mapping $f_\theta: X \to Y$ from the inputs to the machine parameters.

In the most straightforward setting, a loss function can be used that directly compares the deviation in the space of machine parameters e.g., $L(f_\theta(x), y) = \|f_\theta(x) - y\|_2^2$. In certain cases, the comparison is performed in the space of dose distributions according to Equation 6:

$$L(f_\theta(x), y) = \|D(x, y) - D(x, f_\theta(x))\|_2^2 \qquad (6)$$

Figure 8:
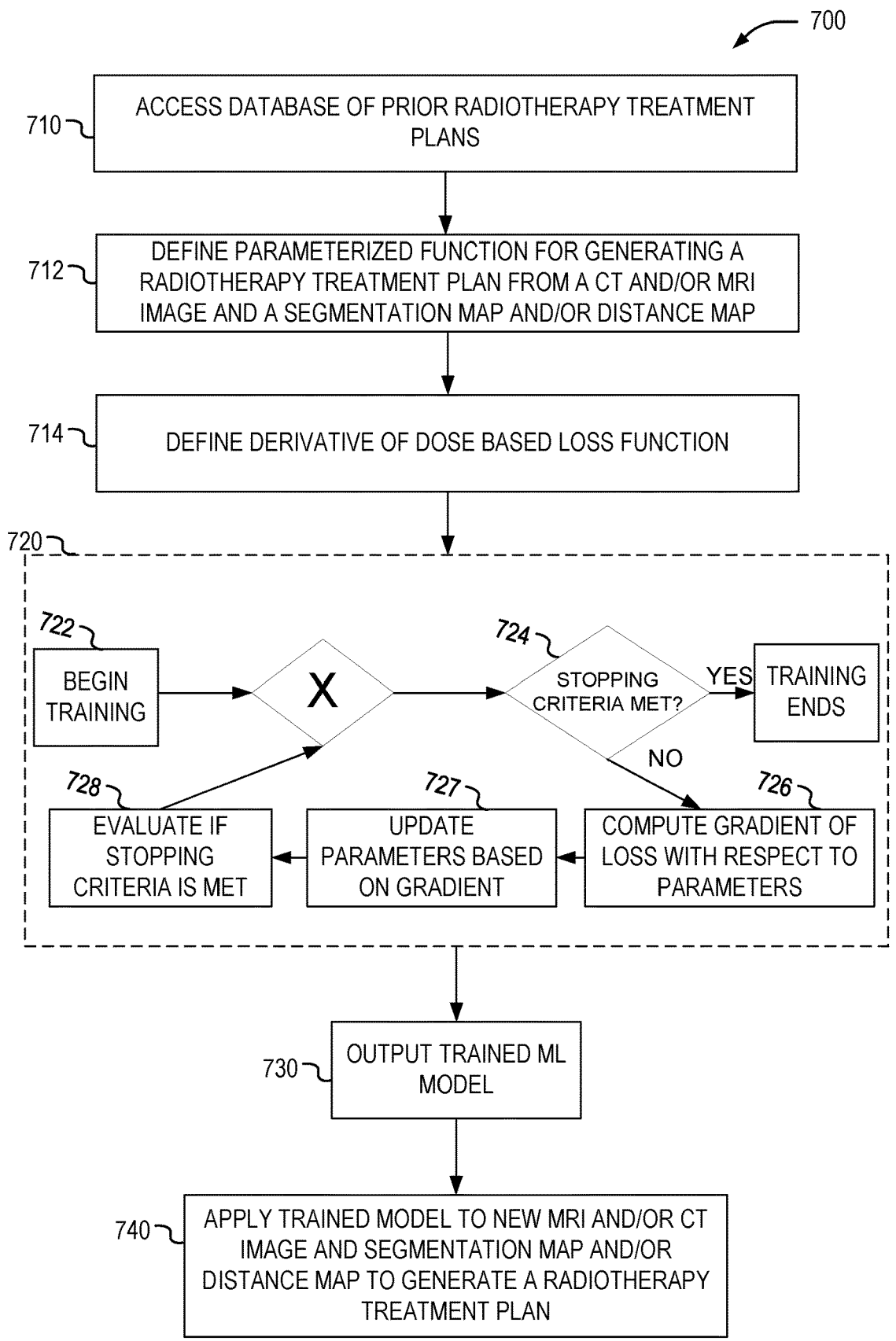

Training such an ML model can be performed in a similar manner as shown and described in FIG. 8.

In some embodiments, an optimization problem can be solved using parameters that are based on a derivative of a dose expression to select irradiation directions. The use of differential dose calculations is similar for beam orientation selection for linear accelerators as it is for isocenter selection for Gamma Knife treatments. A specific example focuses on Gamma Knife and is discussed in connection with FIG. 9.

Leksell Gamma Knife (LGK) is a dedicated system for intracranial stereotactic radiosurgery. The radiation is collimated to create a focus where the radiation from every source converges. At the focus, both the radiation intensity and its gradient become very large. This makes it possible to deliver high radiation doses with minimal damage to surrounding healthy tissue. There may be two ways of tailoring the radiation dose according to the shape and size of the target. First, the patient can be precisely moved (robotically) in relation to the focus, effectively placing the focus in different isocenters. Second, the radiation sources are arranged in eight, independently controlled, sectors. Each sector can be in one of four different collimator states: the 4, 8, or 16 mm or in the beam-off state. For each isocenter position and collimator configuration (e.g., collimator size for each sector), the irradiation time can be specified. This composition is often referred to as a shot.

The large number of degrees of freedom allows sculpting of the dose distribution in unparalleled ways. At the same time, however, it is infeasible to explore them all by means of manual planning. Thus, an inverse planning method is utilized to make the full potential of LGK clinically accessible. Inverse planning methods only require the user to specify what objectives to strive for, and then use mathematical optimization to search for the best possible treatment plan according to these objectives. Typically, a set of isocenters is generated by means of a heuristic, geometric, algorithm. For these isocenters, the dose rate kernel is precomputed and its shape fixed, so that even if an isocenter is moved as part of the optimization, the corresponding dose kernel is simply moved in the same way. In other words, such typical techniques do not take tissue inhomogeneities into account.

In reality, the total dose is given by the superposition of the doses given with all collimator sizes, from all sectors at every isocenter, but for the sake of simplicity only the case with just a single collimator, sector and isocenter (the multidimensional version just consists of replacing the multiplication with a matrix-vector multiplication) is discussed and represented by Equation 7:

$$D(r, r', t) = \psi(r, r')t \qquad (7)$$

where $\psi(r, r')$ is the dose rate at position r due to an isocenter at position r', and t is the irradiation time.

In this example, the loss function (also known as objective function or utility function) of the inverse planning problem would be a function of the parameters $\theta = \{r', t\}$ (radiation parameters), for instance defined by Equation 8:

$$L(r', t) = w_T \int_{V_T} \max(\hat{D}(r) - D(r, r', t), 0) dr + w_O \int_{V_O} \max(D(r, r', t) - \hat{D}(r), 0) dr + |t|, \qquad (8)$$

where $w_T$ and $w_O$ are scalar weight factors that control the importance of giving higher dose than $\hat{D}$ to the target volume $V_T$ and reducing the dose below $\hat{D}$ in an organ at risk volume $V_O$. The |t|-term expresses the desire to keep treatment times short. If the physical constraint is incorporated that the irradiation time is necessarily nonnegative, t≥0, the inverse planning problem can be expressed as the nonlinear, bound constrained, optimization problem of Equation 9:

$$\minimize_{r', t} L(r', t) \qquad (9)$$

$$\text{subject to } t \geq 0$$

This type of optimization problem can be solved using e.g., an iterative gradient-based scheme such as projected (sub) gradient descent:

$$\theta^{(k+1)} = \text{proj}_{t \geq 0}(\theta^{(k)} - \eta g^{(k)}),$$

where $\text{proj}_{t\geq 0}$ is the projection onto the feasible set $t\geq 0$, $\eta \in \mathbb{R}$ is a stepsize and $g^{(k)}$ is any subgradient at $\theta^{(k)}$. The reason subgradients are used in this case is because the particular loss function in Equation (9) is non-differentiable when $D=\hat{D}$. The gradient of the loss with respect to the parameters can be evaluated using the chain rule according to Equation 10:

$$\frac{dL}{dr'} = \frac{dL}{dD}\frac{\partial D}{\partial r'} = \frac{dL}{dD}\left(\frac{\partial \psi}{\partial r'} \cdot t\right), \frac{dL}{dt} = \frac{dL}{dD}\frac{\partial D}{\partial t} = \frac{dL}{dD} \cdot \psi, \quad (10)$$

The gradient of the dose kernel with respect to the isocenter position can be evaluated numerically or by means of automatic differentiation.

A variation of the above is to introduce auxiliary variables s(r) to formulate a smooth optimization problem that is equivalent to Equation (9) but defined in terms of the larger set of variables (r', s). In this modified problem, the loss is expressed by Equation 11:

$$L(r', t, s) = w_T \int_{V_T} s(r)dr + w_o \int_{V_o} s(r)dr + |t|, \quad (10)$$

and the additional set of constraints are defined as follows:

$$0 \leq s(r) \quad r \in V_T,$$
$$\hat{D}(r) - D(r, r', t) \leq s(r) \quad r \in V_T,$$
$$0 \leq s(r) \quad r \in V_O,$$
$$D(r, r', t) - \hat{D}(r) \leq s(r) \quad r \in V_O.$$

This optimization problem of Equation 10 can be solved using higher-order optimization methods, e.g., a Newton method, which makes uses of the second order derivate (Hessian) or using a (quasi-Newton) solver, e.g., sequential quadratic programming (SQP) or an interior point method, that is known to work well even with the type of nonlinear constraints of this problem.

Figure 4:
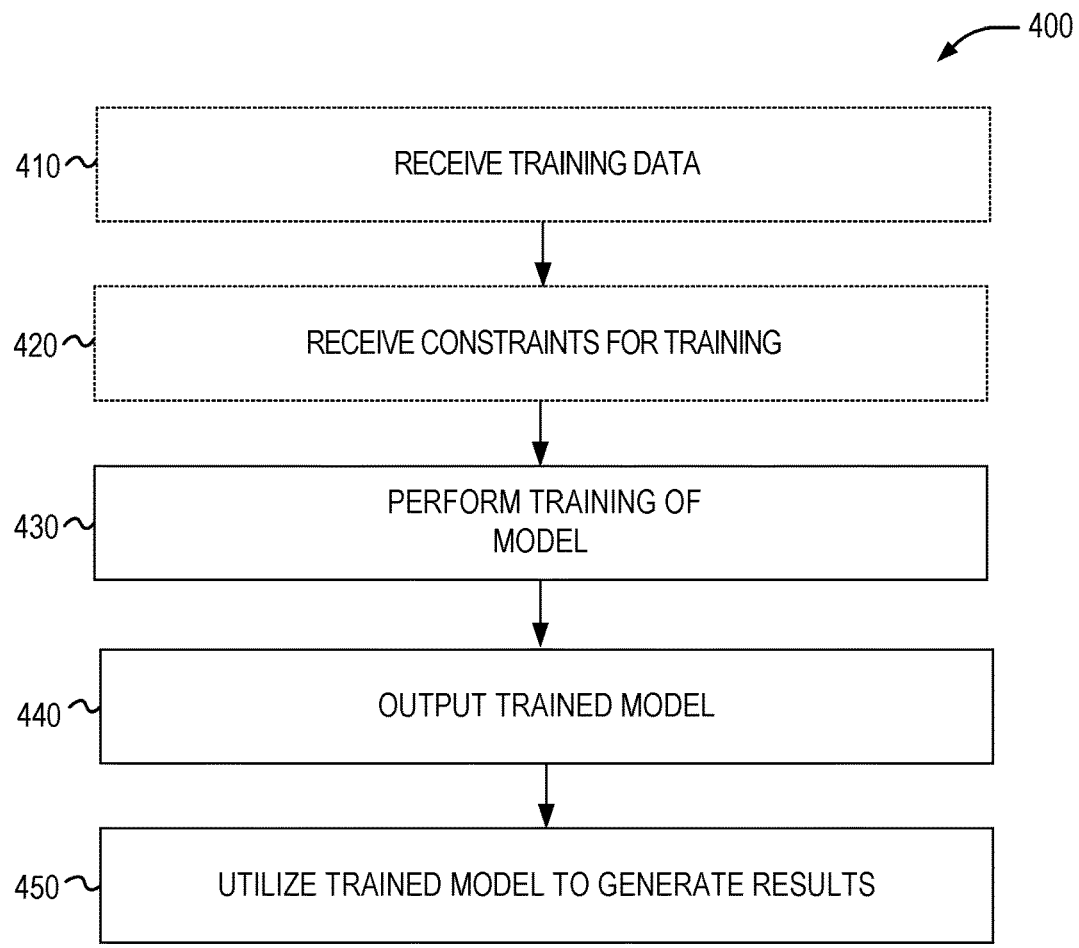
FIGS. 4-9 illustrate flowcharts of exemplary operations for estimating radiotherapy treatment plan parameters based on a derivative of a dose calculation, according to some examples of the disclosure.

FIG. 4 is a flowchart illustrating example operations of the treatment processing logic 120 in performing process 400, according to example embodiments. The process 400 may be embodied in computer-readable instructions for execution by one or more processors such that the operations of the process 400 may be performed in part or in whole by the functional components of the treatment processing logic 120; accordingly, the process 400 is described below by way of example with reference thereto. However, in other embodiments, at least some of the operations of the process 400 may be deployed on various other hardware configurations. The process 400 is therefore not intended to be limited to the treatment processing logic 120 and can be implemented in whole, or in part, by any other component. Some or all of the operations of process 400 can be in parallel, out of order, or entirely omitted.

At operation 410, treatment processing logic 120 receives training data. For example, treatment processing logic 120 receives pairs of a plurality of training radiotherapy treatment plan information and a plurality of training radiotherapy treatment plan parameters; pairs of training MR and/or CBCT images and training sCT images; pairs of training MR, CT, sCT, CBCT images, segmentation and distance maps and training radiotherapy device control points; and pairs of training dose computation functions and training dose distributions.

At operation 420, treatment processing logic 120 receives constraints for training.

At operation 430, treatment processing logic 120 performs training of the model. For example, treatment processing logic 120 may train the ML model parameters 312 (FIG. 3) by minimizing a gradient or derivative of a loss function to which one or more dose computations have been applied that have been estimated based on one or more training radiotherapy treatment plan information and the corresponding training radiotherapy treatment plan parameters. In this way, the ML model is trained to establish a relationship between radiotherapy treatment plan information and one or more radiotherapy treatment plan parameters. The training can be performed in a supervised or unsupervised manner.

At operation 440, treatment processing logic 120 outputs the trained model. For example, the trained model can be output and stored in a memory or parameters of the model can be presented on a display device to a clinician.

At operation 450, treatment processing logic 120 utilizes the trained model to generate results. For example, after each of the machine learning models $\hat{A}_\theta$ (sometimes referred to as $\Lambda_\theta$) is trained, new data 370, including one or more patient input parameters (e.g., radiotherapy treatment plan information), may be received. The trained machine learning technique $\hat{A}_\theta$ may be applied to the new data 370 to generate generated results 380 including one or more estimated radiotherapy treatment plan parameters.

Figure 5:
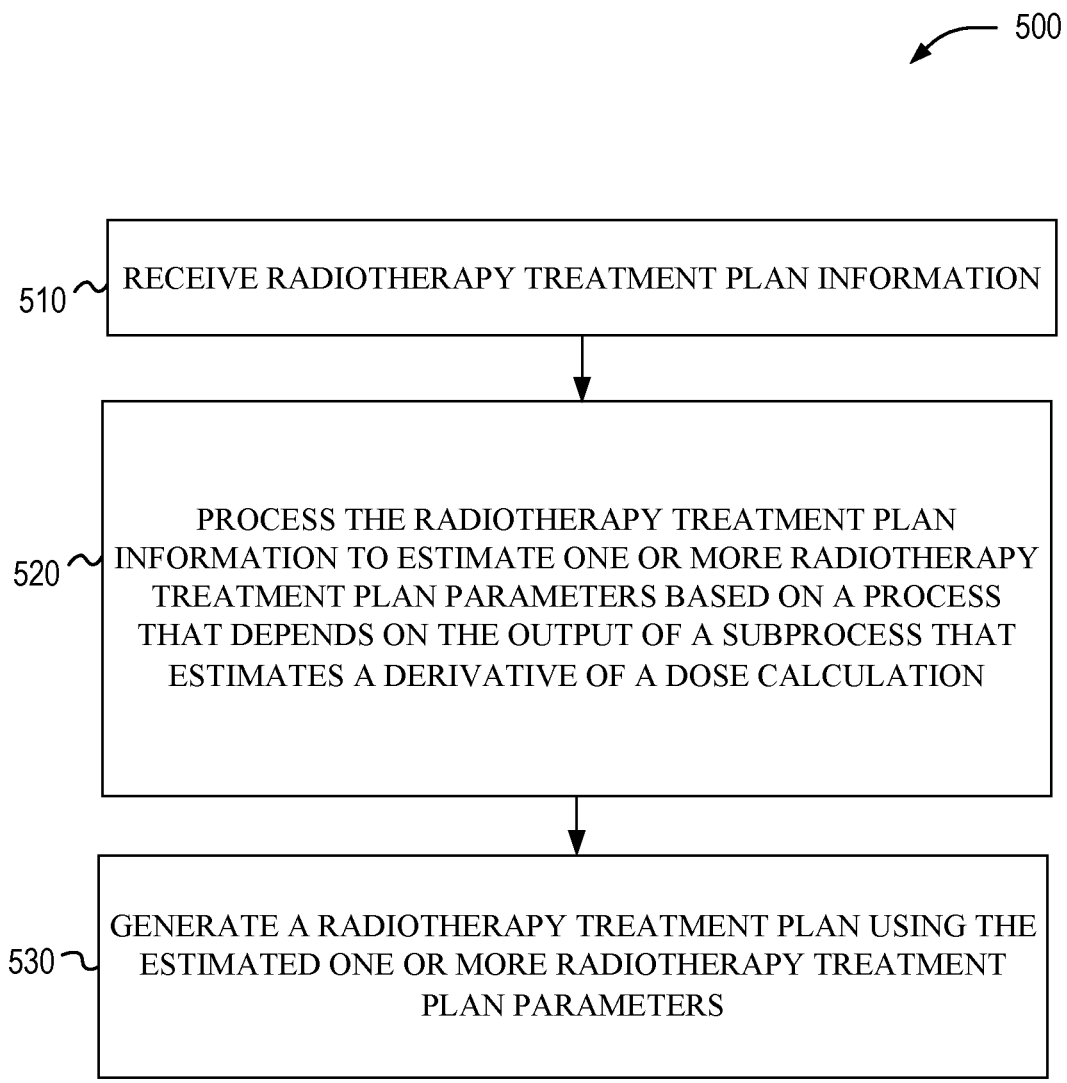

FIG. 5 is a flowchart illustrating example operations of the treatment processing logic 120 in performing process 500, according to example embodiments. The process 500 may be embodied in computer-readable instructions for execution by one or more processors such that the operations of the process 500 may be performed in part or in whole by the functional components of the treatment processing logic 120; accordingly, the process 500 is described below by way of example with reference thereto. However, in other embodiments, at least some of the operations of the process 500 may be deployed on various other hardware configurations. The process 500 is therefore not intended to be limited to the treatment processing logic 120 and can be implemented in whole, or in part, by any other component. Some or all of the operations of process 500 can be in parallel, out of order, or entirely omitted.

At operation 510, treatment processing logic 120 receives a radiotherapy treatment plan information.

At operation 520, treatment processing logic 120 processes the radiotherapy treatment plan information to estimate one or more radiotherapy treatment plan parameters based on a process that depends on the output of a subprocess that estimates a derivative of a dose calculation.

At operation 530, treatment processing logic 120 generates a radiotherapy treatment plan using the estimated one or more radiotherapy treatment plan parameters.

Figure 6:
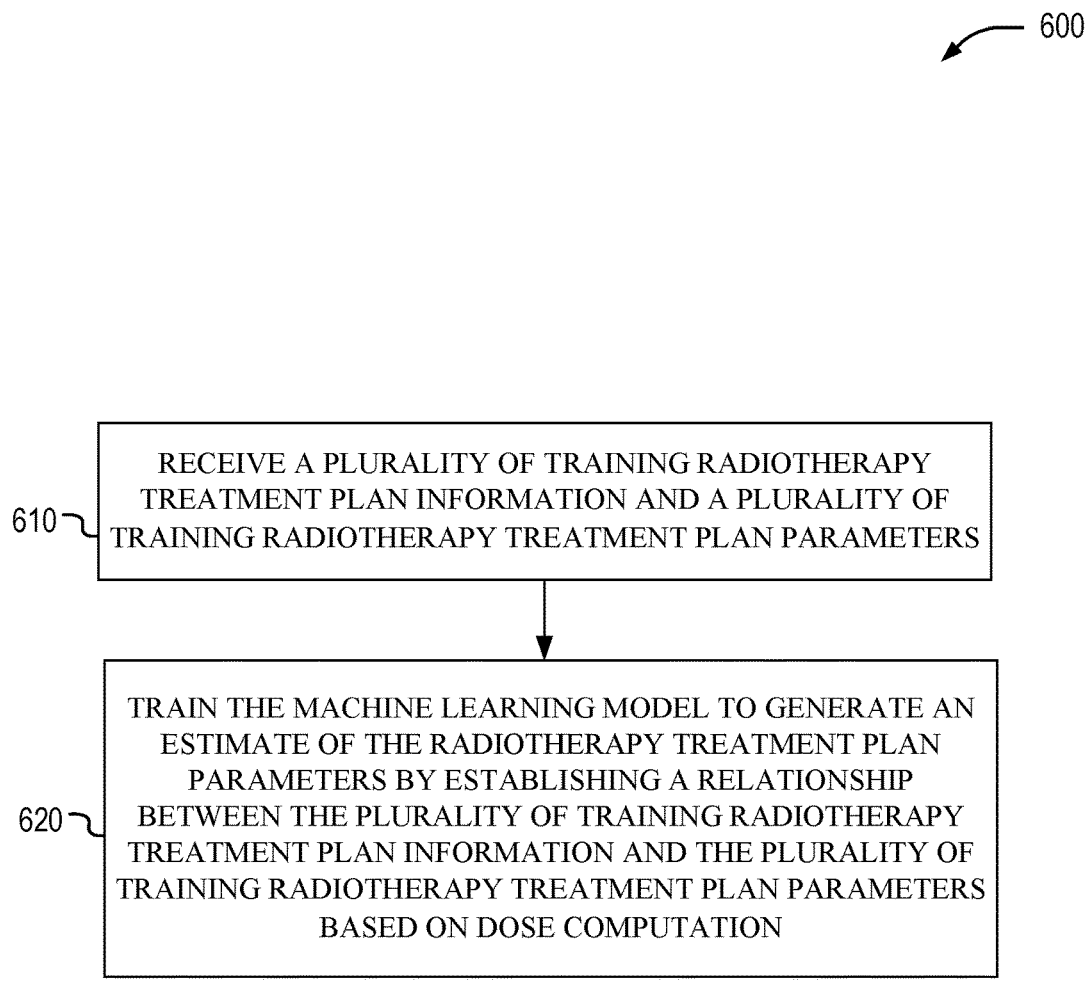

FIG. 6 is a flowchart illustrating example operations of the treatment processing logic 120 in performing a process 600, according to example embodiments. The process 600 may be embodied in computer-readable instructions for execution by one or more processors such that the operations of the process 600 may be performed in part or in whole by the functional components of the treatment processing logic 120; accordingly, the process 600 is described below by way of example with reference thereto. However, in other embodiments, at least some of the operations of the process 600 may be deployed on various other hardware configurations. The process 600 is therefore not intended to be limited to the treatment processing logic 120 and can be implemented in whole, or in part, by any other component. Some or all of the operations of process 600 can be in parallel, out of order, or entirely omitted.

At operation 610, treatment processing logic 120 receives a plurality of training radiotherapy treatment plan information and a plurality of training radiotherapy treatment plan parameters.

At operation 620, treatment processing logic 120 trains the machine learning model to generate an estimate of the radiotherapy treatment plan parameters by establishing a relationship between the plurality of training radiotherapy treatment plan information and the plurality of training radiotherapy treatment plan parameters based on dose computation.

Figure 7:
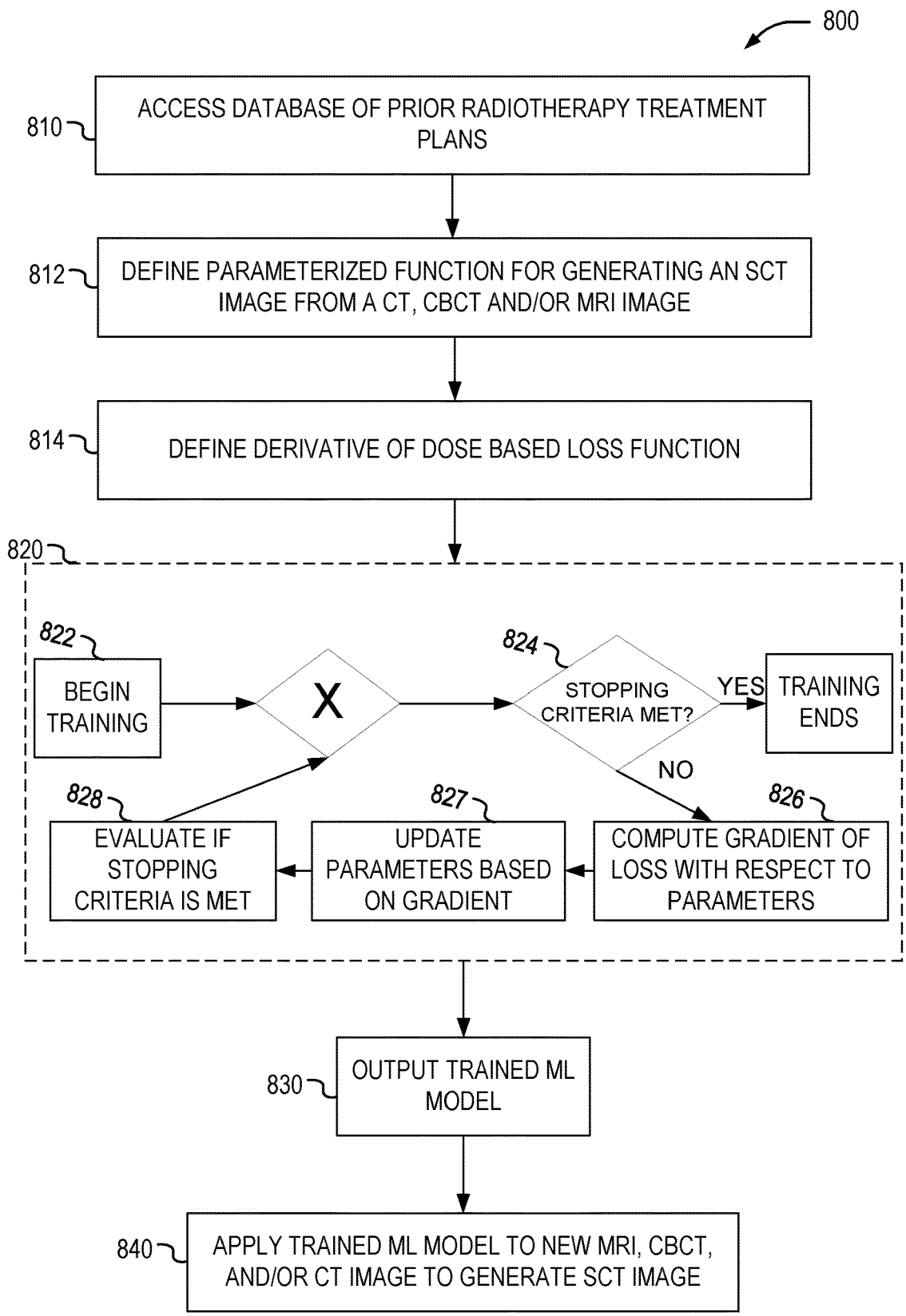

FIG. 7 is a flowchart illustrating example operations of the treatment processing logic 120 in performing a process 700, according to example embodiments. The process 700 may be embodied in computer-readable instructions for execution by one or more processors such that the operations of the process 700 may be performed in part or in whole by the functional components of the treatment processing logic 120; accordingly, the process 700 is described below by way of example with reference thereto. However, in other embodiments, at least some of the operations of the process 700 may be deployed on various other hardware configurations. The process 700 is therefore not intended to be limited to the treatment processing logic 120 and can be implemented in whole, or in part, by any other component. Some or all of the operations of process 700 can be in parallel, out of order, or entirely omitted.

At operation 710, treatment processing logic 120 accesses a database of prior radiotherapy treatment plans.

At operation 712, treatment processing logic 120 defines a parameterized function (e.g., an ML model) for generating an sCT image from a CT, CBCT, and/or MRI image.

At operation 714, treatment processing logic 120 define a derivative of dose based loss function. For example, the treatment processing logic 120 can obtain the loss function defined by Equation 4.

At operation 720, treatment processing logic 120 trains the parametrized function. For example, the treatment processing logic 120 operates on batches of training CT, CBCT, and/or MRI images and their corresponding training sCT images to train the ML model based on the loss function defined by Equation 4.

At operation 722, treatment processing logic 120 begins training the parameterized function. For example, the treatment processing logic 120 obtains a first batch of training CT, CBCT, and/or MRI images and their corresponding training sCT images. The treatment processing logic 120 applies the ML model to the first batch of training CT, CBCT, and/or MRI images to estimate an intermediate sCT image. The treatment processing logic 120 computes a derivative or gradient of a first dose based on the intermediate sCT image and a second dose based on the training sCT image. The first and second dose derivatives or gradients are applied to the loss function of Equation 4.

At operation 724, treatment processing logic 120 determines if stopping criteria for training the parameterized function has been met. If the stopping criteria has been met, the treatment processing logic 120 proceeds to end training and otherwise the treatment processing logic 120 proceeds to operation 726.

At operation 726, treatment processing logic 120 computes a gradient or derivative of loss with respect to parameters of the parameterized function.

At operation 727, treatment processing logic 120 updates parameters of the parameterized function based on the gradient or derivative of the loss.

At operation 728, treatment processing logic 120 evaluates if stopping criteria has been met. If not, another batch of training data is accessed and another iteration of training the ML model is performed.

At operation 730, treatment processing logic 120 outputs the trained ML model.

At operation 740, treatment processing logic 120 applies the trained ML model to a new MRI, CBCT, and/or CT image to generate an sCT image.

FIG. 8 is a flowchart illustrating example operations of the treatment processing logic 120 in performing a process 800, according to example embodiments. The process 800 may be embodied in computer-readable instructions for execution by one or more processors such that the operations of the process 800 may be performed in part or in whole by the functional components of the treatment processing logic 120; accordingly, the process 800 is described below by way of example with reference thereto. However, in other embodiments, at least some of the operations of the process 800 may be deployed on various other hardware configurations. The process 800 is therefore not intended to be limited to the treatment processing logic 120 and can be implemented in whole, or in part, by any other component. Some or all of the operations of process 800 can be in parallel, out of order, or entirely omitted.

At operation 810, treatment processing logic 120 accesses a database of prior radiotherapy treatment plans.

At operation 812, treatment processing logic 120 defines parameterized function for generating a radiotherapy treatment plan from a CT and/or MRI image and a segmentation map and/or distance map.

At operation 814, treatment processing logic 120 define derivative of dose based loss function. For example, the treatment processing logic 120 can obtain the loss function defined by Equation 6.

At operation 820, treatment processing logic 120 trains the parametrized function. For example, the treatment processing logic 120 operates on batches of training CT and/or MRI images and segmentation maps and/or distance maps and their corresponding training radiotherapy treatment plans to train the ML model based on the loss function defined by Equation 6.

At operation 822, treatment processing logic 120 begins training the parameterized function. For example, the treatment processing logic 120 obtains a first batch of training CT and/or MRI images and segmentation maps and/or distance maps and their corresponding training radiotherapy treatment plans. The treatment processing logic 120 applies the ML model to the first batch of training CT and/or MRI images and segmentation maps and/or distance maps to estimate an intermediate radiotherapy treatment plan. The treatment processing logic 120 computes a derivative or gradient of a first dose based on the intermediate radiotherapy treatment plan and a second dose based on the training radiotherapy treatment plan. The first and second dose derivatives or gradients are applied to the loss function of Equation 6.

At operation 824, treatment processing logic 120 determines if stopping criteria for training the parameterized function has been met. If the stopping criteria has been met, the treatment processing logic 120 proceeds to end training and otherwise the treatment processing logic 120 proceeds to operation 826.

At operation 826, treatment processing logic 120 computes a gradient or derivative of loss with respect to parameters of the parameterized function.

At operation 827, treatment processing logic 120 updates parameters of the parameterized function based on the gradient or derivative of the loss.

At operation 828, treatment processing logic 120 evaluates if stopping criteria has been met. If not, another batch of training data is accessed and another iteration of training the ML model is performed.

At operation 830, treatment processing logic 120 outputs the trained ML model.

At operation 840, treatment processing logic 120 applies the trained ML model to a new MRI and/or CT image and segmentation map and/or distance map to generate a radiotherapy treatment plan.

Figure 9:
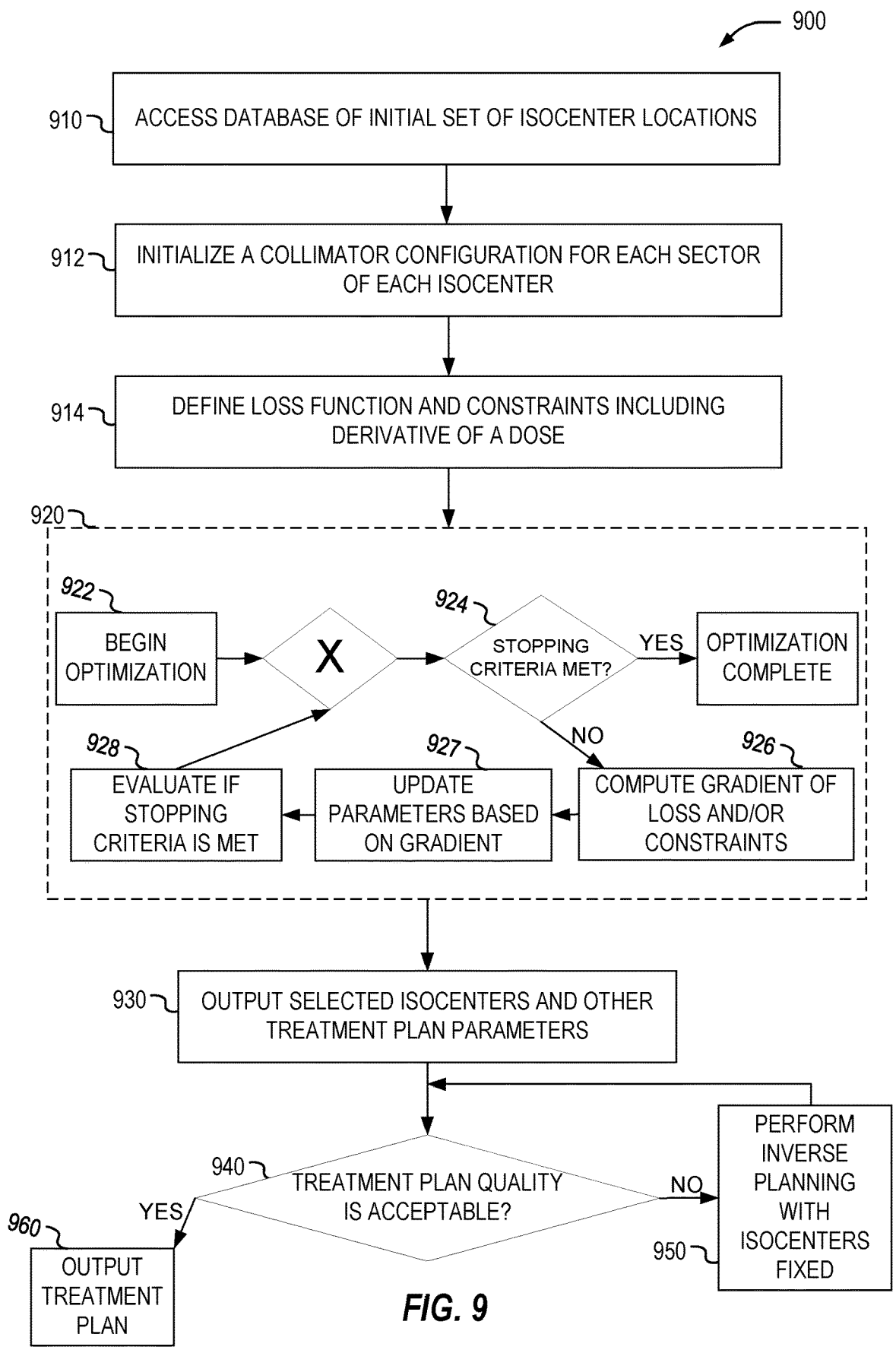

FIG. 9 is a flowchart illustrating example operations of the treatment processing logic 120 in performing a process 900, according to example embodiments. The process 900 may be embodied in computer-readable instructions for execution by one or more processors such that the operations of the process 900 may be performed in part or in whole by the functional components of the treatment processing logic 120; accordingly, the process 900 is described below by way of example with reference thereto. However, in other embodiments, at least some of the operations of the process 900 may be deployed on various other hardware configurations. The process 900 is therefore not intended to be limited to the treatment processing logic 120 and can be implemented in whole, or in part, by any other component. Some or all of the operations of process 900 can be in parallel, out of order, or entirely omitted.

At operation 910, treatment processing logic 120 accesses a database of an initial set of isocentre locations.

At operation 912, treatment processing logic 120 initializes a collimator configuration for each sector of each isocenter.

At operation 914, treatment processing logic 120 defines a loss function and constraints including a derivative of a dose expression for an optimization problem. For example, the treatment processing logic 120 obtains the loss function of Equation 8 or 10.

At operation 920, treatment processing logic 120 optimizes the optimization problem.

At operation 922, treatment processing logic 120 begins optimization of the optimization problem. For example, the treatment processing logic 120 begins solving the optimization problem using iterative gradient decent.

At operation 924, treatment processing logic 120 determines if stopping criteria for optimizing the optimization problem has been met. If the stopping criteria has been met, the treatment processing logic 120 proceeds to end optimization and otherwise the treatment processing logic 120 proceeds to operation 926.

At operation 926, treatment processing logic 120 computes a gradient or derivative of loss and/or constraints of the optimization problem.

At operation 927, treatment processing logic 120 updates parameters of the optimization problem based on the gradient or derivative.

At operation 928, treatment processing logic 120 evaluates if stopping criteria has been met.

At operation 930, treatment processing logic 120 outputs the selected isocenters and other treatment plan parameters.

At operation 940, treatment processing logic 120 determines if the treatment plan quality is acceptable (e.g., satisfies a quality threshold). If the quality is acceptable, the treatment processing logic 120 proceeds to output the treatment plan at operation 960 and otherwise the treatment processing logic 120 proceeds to operation 950.

At operation 950, treatment processing logic 120 performs inverse planning with isocenters being fixed.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 232, perform or implement the training or prediction operations from FIG. 3, operate the trained treatment model 360, perform or implement the operations of the flowcharts for processes 400-900, or perform any one or more of the other methodologies discussed herein (e.g., as part of treatment processing logic 120). In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other beneficial results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matters contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials, and example parameters, functions, and implementations described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method comprising:
   accessing a database of training data comprising prior radiotherapy treatment plans;
   iteratively training a machine learning model to generate one or more synthetic computerized tomography (sCT) images from one or more medical images that are received by the machine learning model based on a loss function, the one or more medical images being selected from one or more batches of the training data comprising the prior radiotherapy treatment plans over each iteration;
   during the iterative training of the machine learning model computing a derivative of a dose based on the one or more sCT images;
   computing a gradient of the loss function based on the derivative of the dose;

updating one or more parameters of the machine learning model based on the computed gradient of the loss function; and terminating the iterative training of the machine learning model to output the trained machine learning model in response to determining that a stopping criterion is met.

2. The method of claim 1, further comprising applying the trained machine learning model to a new medical image to generate a new sCT image corresponding to the new medical image.

3. The method of claim 1, wherein training the machine learning model comprises:
obtaining a first batch of data comprising training medical images and training sCT images corresponding to the training medical images; and
applying the machine learning model to the first batch of data to estimate an intermediate sCT image.

4. The method of claim 3, further comprising:
computing a derivative or gradient of a first dose based on the intermediate sCT image;
computing a derivative or gradient of a second dose based on a given one of the training sCT images; and
computing the loss function based on the derivative or gradients of the first and second doses.

5. The method of claim 1, further comprising training another machine learning model for generating a radiotherapy treatment plan from a medical image and a segmentation map or distance map.

6. The method of claim 1, further comprising:
processing radiotherapy treatment plan information to estimate one or more radiotherapy treatment plan parameters based on a process that depends on an output of a subprocess that estimates a derivative of a dose calculation, wherein the derivative of the dose calculation is used in the machine learning model, wherein the derivative of the dose calculation is computed with respect to at least one of one or more radiation parameters or one or more geometry parameters of a radiotherapy treatment device.

7. The method of claim 6, wherein the machine learning model is trained, based on a plurality of training dose calculations, to establish a relationship between a plurality of training radiotherapy treatment plan information and a plurality of training radiotherapy treatment plan parameters.

8. The method of claim 1, wherein the machine learning model includes a deep neural network, wherein the one or more medical images comprise at least one of a training magnetic resonance (MR) image, a training cone-beam computed tomography (CBCT) image, a training computed tomography (CT) image.

9. A non-transitory computer-readable medium comprising non-transitory computer-readable instructions, the computer-readable instructions comprising instructions that, when executed by one or more processors, program the one or more processors to perform operations comprising:
accessing a database of training data comprising prior radiotherapy treatment plans;
iteratively training a machine learning model to generate one or more synthetic computerized tomography (sCT) images from one or more medical images that are received by the machine learning model based on a loss function, the one or more medical images being selected from one or more batches of the training data comprising the prior radiotherapy treatment plans over each iteration;
during the iterative training of the machine learning model computing a derivative of a dose based on the one or more sCT images;
computing a gradient of the loss function based on the derivative of the dose;
updating one or more parameters of the machine learning model based on the computed gradient of the loss function; and
terminating the iterative training of the machine learning model to output the trained machine learning model in response to determining that a stopping criterion is met.

10. The non-transitory computer-readable medium of claim 9, wherein the operations further comprise applying the trained machine learning model to on a new medical image to generate a new sCT image corresponding to the new medical image.

11. The non-transitory computer-readable medium of claim 9, wherein training the machine learning model comprises:
obtaining a first batch of data comprising training medical images and training sCT images corresponding to the training medical images; and
applying the machine learning model to the first batch of data to estimate an intermediate sCT image.

12. The non-transitory computer-readable medium of claim 11, wherein the operations further comprise:
computing a derivative or gradient of a first dose based on the intermediate sCT image;
computing a derivative or gradient of a second dose based on a given one of the training sCT images; and
computing the loss function based on the derivative or gradients of the first and second doses.

13. A system comprising:
a memory for storing instructions; and
one or more processors for executing the instructions stored in the memory for performing operations comprising:
accessing a database of training data comprising prior radiotherapy treatment plans;
iteratively training a machine learning model to generate one or more synthetic computerized tomography (sCT) images from one or more medical images that are received by the machine learning model based on a loss function, the one or more medical images being selected from one or more batches of the training data comprising the prior radiotherapy treatment plans over each iteration;
during the iterative training of the machine learning model computing a derivative of a dose based on the one or more sCT images;
computing a gradient of the loss function based on the derivative of the dose;
updating one or more parameters of the machine learning model based on the computed gradient of the loss function; and
terminating the iterative training of the machine learning model to output the trained machine learning model in response to determining that a stopping criterion is met.

14. The system of claim 13, wherein the operations further comprise applying the trained machine learning model to a new medical image to generate a new sCT image corresponding to the new medical image.

15. The system of claim 13, wherein training the machine learning model comprises:
obtaining a first batch of data comprising training medical images and training sCT images corresponding to the training medical images; and applying the machine learning model to the first batch of data to estimate an intermediate sCT image.

16. The system of claim 15, wherein the operations further comprise:
   computing a derivative or gradient of a first dose based on the intermediate sCT image;
   computing a derivative or gradient of a second dose based on a given one of the training sCT images; and
   computing the loss function based on the derivative or gradients of the first and second doses.

* * * * *